(12) United States Patent
Lee et al.

(10) Patent No.: US 10,405,788 B2
(45) Date of Patent: Sep. 10, 2019

(54) CATHETER-GUIDED MINIATURIZED WIRELESS VISCERA COMPLIANCE SENSOR SYSTEM

(71) Applicant: KOREA ADVANCED INSTITUTE OF SCIENCE AND TECHNOLOGY, Daejon (KR)

(72) Inventors: Hyunjoo Jenny Lee, Daejon (KR); Hyojung Kim, Daejon (KR); Sangchul Lee, Seoul (KR)

(73) Assignee: KOREA ADVANCED INSTITUTE OF SCIENCE AND TECHNOLOGY, Daejon (KR)

( * ) Notice: Subject to any disclaimer, the term of this patent is extended or adjusted under 35 U.S.C. 154(b) by 0 days.

(21) Appl. No.: 15/937,786

(22) Filed: Mar. 27, 2018

(65) Prior Publication Data
US 2018/0303398 A1    Oct. 25, 2018

(30) Foreign Application Priority Data

Apr. 25, 2017 (KR) .................. 10-2017-0052962

(51) Int. Cl.
*A61B 5/00* (2006.01)
*A61B 5/20* (2006.01)
(Continued)

(52) U.S. Cl.
CPC .............. *A61B 5/202* (2013.01); *A61B 5/04* (2013.01); *C08K 3/16* (2013.01); *C08L 89/00* (2013.01);
(Continued)

(58) Field of Classification Search
CPC ..... A61B 5/6853; A61B 5/205; A61B 5/6852; A61B 5/14539; A61B 5/036;
(Continued)

(56) References Cited

U.S. PATENT DOCUMENTS 4,612,939 A * 9/1986 Robertson ............. A61B 5/205
600/135
5,865,801 A * 2/1999 Houser .................. A61B 5/036
600/488

(Continued)

FOREIGN PATENT DOCUMENTS

KR    20130138763 A    12/2013

OTHER PUBLICATIONS

Jihye Lee et al., "Effect of Silk in Silk/PLGA Hybrid Films on Attachment and Proliferation of Human Aortic Endothelial Cells," Polymer (Korea), vol. 37, No. 2, pp. 127-134, 8 pgs.
(Continued)

*Primary Examiner* — May A Abouelela
(74) *Attorney, Agent, or Firm* — Morgan, Lewis & Bockius LLP

(57) ABSTRACT

Disclosed herein is a sensor attached to viscera to measure a change in length, in which the sensor includes a first layer having a first surface attached to the viscera and a second surface opposite to the first surface, a second layer having a third surface attached to the second surface and a fourth surface opposite to the third surface and expanded or contracted as the viscera is expanded or contracted, and a third layer having a fifth surface attached to the fourth surface and a sixth surface opposite to the fifth surface and attached to a catheter, and the first layer to the third layer are a film including silk fibroin and a calcium compound.

15 Claims, 19 Drawing Sheets

(51) Int. Cl.
*A61B 5/04* (2006.01)
*C08K 3/16* (2006.01)
*C09J 189/00* (2006.01)
*C08L 89/00* (2006.01)

(52) U.S. Cl.
CPC ............ *C09J 189/00* (2013.01); *A61B 5/6852* (2013.01); *A61B 2562/16* (2013.01); *C08K 2003/162* (2013.01)

(58) Field of Classification Search
CPC ............ A61B 2562/0247; A61B 5/202; A61B 5/0215; A61B 5/0538; A61B 5/4238; A61B 2018/00517; A61B 5/04884; A61B 5/6874; A61B 18/1492; A61B 17/12136
USPC ............... 600/300, 409, 373, 561, 587, 595; 604/174; 606/108
See application file for complete search history.

(56) References Cited

U.S. PATENT DOCUMENTS

| | | | | |
|---|---|---|---|---|
| 6,293,923 B1* | 9/2001 | Yachia | ............... | A61F 2/0027 600/29 |
| 6,416,504 B2* | 7/2002 | Mosel | ............... | A61B 5/202 600/202 |
| 8,109,883 B2* | 2/2012 | Meyer | ............... | A61B 5/0011 600/300 |
| 8,821,429 B2* | 9/2014 | Vargas | ............... | A61F 5/0036 604/104 |
| 9,028,406 B2* | 5/2015 | Addington | ......... | A61B 5/04882 600/300 |
| 9,028,407 B1* | 5/2015 | Bennett-Guerrero | ......... | A61B 5/1121 600/301 |
| 9,655,555 B2* | 5/2017 | Burnett | ............... | A61B 5/0215 |
| 2002/0111586 A1* | 8/2002 | Mosel | ............... | A61B 5/202 604/174 |
| 2003/0114735 A1* | 6/2003 | Silver | ............... | A61B 5/0031 600/300 |
| 2008/0081954 A1* | 4/2008 | Meyer | ............... | A61B 5/0011 600/300 |
| 2010/0094116 A1* | 4/2010 | Silverstein | ............... | A61B 5/06 600/409 |
| 2010/0222802 A1* | 9/2010 | Gillespie, Jr. | ......... | A61B 90/02 606/192 |
| 2012/0265049 A1* | 10/2012 | Iglesias | ............... | A61M 25/04 600/409 |
| 2013/0030262 A1* | 1/2013 | Burnett | ............... | A61B 5/0215 600/309 |
| 2013/0231584 A1* | 9/2013 | Burnett | ............... | A61B 5/036 600/561 |
| 2013/0253343 A1* | 9/2013 | Waldhauser | ......... | A61B 5/0215 600/486 |
| 2015/0057519 A1* | 2/2015 | Ben-David | ......... | A61B 5/6853 600/373 |
| 2015/0320357 A1* | 11/2015 | Kuraguntla | ............... | G01F 1/00 600/505 |
| 2015/0366498 A1* | 12/2015 | Choi | ............... | A61B 5/205 600/373 |
| 2016/0029998 A1* | 2/2016 | Brister | ............... | A61B 5/6853 600/424 |
| 2016/0183819 A1* | 6/2016 | Burnett | ............... | A61B 5/6853 600/309 |
| 2016/0331294 A1* | 11/2016 | Imran | ............... | A61B 5/205 |
| 2018/0177458 A1* | 6/2018 | Burnett | ............... | A61B 5/01 |

OTHER PUBLICATIONS

Korea Advanced Institute of Science and Technology, Notice of Office Action, Application No. 10-2017-0052962, dated Jun. 29, 2017, 5 pgs.

Korea Advanced Institute of Science and Technology, Notice of Allowance, Application No. 10-2017-0052962, dated Sep. 21, 2017, 3 pgs.

* cited by examiner

CATHETER-GUIDED MINIATURIZED WIRELESS VISCERA COMPLIANCE SENSOR SYSTEM

CROSS-REFERENCE TO RELATED APPLICATION

This application is based on and claims the benefit of priority to Korean Patent Application No. 10-2017-0052962, filed on Apr. 25, 2017 in the Korean Intellectual Property Office, the disclosure of which is incorporated herein in its entirety by reference.

TECHNICAL FIELD

The present disclosure relates to a sensor attached to viscera by a catheter to measure viscera compliance.

BACKGROUND

Since World entered an aging society in 2007, World is becoming the fastest aging in the world. The proportion of people aged 65 and older is expected to reach 24.3% in 2030. By the 1960s to 1970s, dysuria such as irritable bladder, urinary incontinence, prostatic hypertrophy, and neurogenic bladder are rising sharply. Therefore, as World enters the aging society, the number of patients with dysuria in Korea is expected to rise sharply. In addition, the number of patients with dysuria such as a bladder muscle function in charge of storing and discharging urine and urinary incontinence causing an unintended urination phenomenon due to abnormality of a nervous system is rapidly increasing worldwide.

In the past, urodynamic studies such as compliance, a leak point pressure, sensory enhancement, and a bladder volume have been conducted to diagnose the dysuria. An internal volume and a pressure of a bladder have to be measured during the check of the bladder function. However, the existing urodynamic study has checked the bladder function by artificially filling the bladder with about 400 cc of water for 30 to 60 minutes using a catheter. The existing urodynamic study has a problem in that a patient feels a great deal of pain over the check period and even the check period is short as up to one hour.

In order to solve the above problem, an apparatus for inserting a sensor into a bladder to carry out the check has been used. However, there is a problem in that a surgical procedure is required to insert and remove the apparatus.

SUMMARY

The present disclosure has been made to solve the above-mentioned problems occurring in the prior art while advantages achieved by the prior art are maintained intact.

An aspect of the present disclosure provides measurement of viscera compliance without performing a surgical procedure by using a sensor that can be inserted into the viscera by a catheter.

Another aspect of the present disclosure provides measurement of elements required to diagnose diseases while minimizing a patient's pain because a sensor can be removed without a surgical procedure by having biodegradability.

According to an exemplary embodiment of the present disclosure, a film used for a sensor attached to inner wall of viscera to measure a change in compliance of the viscera includes: silk fibroin and a calcium compound.

According to an exemplary embodiment of the present disclosure, a sensor attached to inner wall of viscera to measure a change in compliance of the viscera includes: a first layer having a first surface attached to the inner wall of the viscera and a second surface opposite to the first surface; a second layer having a third surface attached to the second surface and a fourth surface opposite to the third surface and expanded or contracted as the viscera is expanded or contracted; and a third layer having a fifth surface attached to the fourth surface and a sixth surface opposite to the fifth surface and attached to a catheter, in which the first layer to the third layer may be a film including silk fibroin and a calcium compound.

According to still another exemplary embodiment of the present disclosure, a method for measuring compliance of viscera performed by a detection apparatus includes: transmitting a signal to a sensor attached to inner wall of the viscera; receiving the signal reflected from the sensor; and measuring the compliance of the viscera to which the sensor is attached based on the received signal, in which the sensor may include a first layer having a first surface attached to the viscera and a second surface opposite to the first surface, a second layer having a third surface attached to the second surface and a fourth surface opposite to the third surface and expanded or contracted as the viscera is expanded or contracted; and a third layer having a fifth surface attached to the fourth surface and a sixth surface opposite to the fifth surface and attached to a catheter, and the first layer to the third layer may include silk fibroin and a calcium compound.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
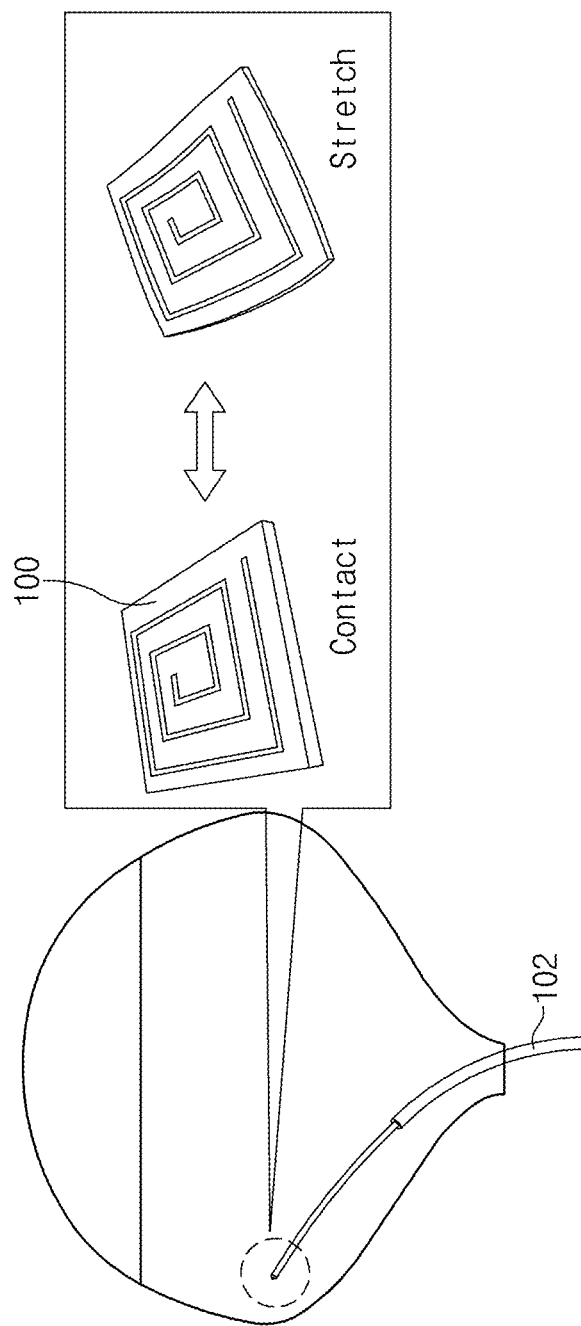
FIG. 1 is a diagram schematically illustrating a use example of a sensor according to an exemplary embodiment of the present disclosure.

Hereinafter, various embodiments of the present disclosure will be described in detail with reference to the accompanying drawings. Throughout the accompanying drawings of the present specification, the same components will be denoted by the same reference numerals, and an overlapped description thereof will be omitted.

Specifically structural and functional descriptions of various embodiments of the present disclosure disclosed in the present specification or the present application are illustrated to describe embodiments of the present disclosure and therefore, various embodiments of the present disclosure may be practiced in various forms and are not to be construed as being limited to the embodiments of the present disclosure disclosed in the present specification.

In various embodiments, expressions such as "first" and "second", "1st", and "2nd" may represent various components without regard to order and/or importance and do not limit the corresponding components. For example, the 'first' component may be named the 'second' component and the 'second' component may also be similarly named the 'first' component, without departing from the scope of the present disclosure.

The terminologies used herein is for the purpose of describing particular embodiments only and may not be intended to limit the scope of other embodiments. Singular forms may be intended to include plural forms unless the context clearly indicates otherwise.

It is to be understood that all the terms used in the present specification including technical and scientific terms have the same meanings as those that are generally understood by those skilled in the art. Terms defined in a general dictionary can be interpreted as having the same or similar meaning as the contextual meanings of the related art and unless explicitly defined herein, are not interpreted as an ideal or excessively formal meaning. In some cases, the terms defined herein may not be construed to exclude embodiments of the present disclosure.

FIG. 1 is a diagram schematically illustrating a use example of a sensor according to an exemplary embodiment of the present disclosure.

As illustrated in FIG. 1, a sensor 100 according to an exemplary embodiment of the present disclosure may be attached to a catheter 102 to be inserted into viscera. Here, the viscera may be, for example, a bladder, a womb, a stomach, an intestine, or the like. The sensor 100 may basically be configured of at least three film layers. Further, the sensor 100 may be configured of four film layers. A first layer of the three film layers of the sensor 100 is a layer attached to inner wall of viscera, a second layer thereof is expanded and contracted according to an expansion or contraction of the viscera to induce a change in a reflected signal to a received signal, and a third layer is a layer attached to a catheter. Further, the sensor 100 may further include a fourth layer which is a circuit layer between the second layer and the third layer. In addition, at least two metals, for example, gold, may be inserted into the second layer. In addition, at least one capacitor may be included in the fourth layer and a circuit for measuring resistance due to the expansion or contraction of the second layer may be inserted therein.

The sensor 100 attached to the catheter 102 is detached from the catheter 102 after attached to the viscera. The sensor 100 attached to the viscera is expanded or contracted in response to a change in length due to the expansion or contraction of the viscera.

Depending on the expansion or contraction, positions of at least two metals inserted into the second layer of the sensor 100 are changed. If a signal is transmitted from the outside of the body to the sensor 100, the metals reflect the signal. The reflected signal will be changed in response to a change in position of the metal, and a change in length of the sensor 100 may be measured by the signal changed in response to the change of the position of the metal. It is possible to measure how much the corresponding viscera is expanded or contracted based on the change in length of the sensor 100.

Unlike the method of inserting a metal into a second layer, however, there is a method for interposing a fourth layer between a second layer and a third layer to measure resistance changed in response to expansion or contraction of the second layer. The circuit included in the fourth layer has a structure that can measure and transmit the resistance of the second layer, which can easily be derived by a person skilled in the art. Therefore, a detailed description of the circuit will be omitted.

In addition, the first to fourth layers configuring the sensor 100 each have adhesive property, stretchability, biodegradability, conductivity, and patternable possibility.

In addition, the first to fourth layers configuring the sensor 100 each are a film made of a silk fibroin and a calcium compound.

Next, the film configuring the sensor 100 will be described.

The film configuring the sensor 100 is a composition made of the silk fibroin and the calcium compound.

A method for producing silk fibroin and a calcium compound according to an exemplary embodiment of the present disclosure is as follows.

Degummed silk fibroin and the calcium compound (e.g., calcium chloride) containing calcium ions corresponding to a specific weight ratio are put in a solvent having a carboxyl group (e.g., formic acid) and completely dissolved.

Then, the degummed silk fibroin corresponding to the above weight ratio is added to the solvent in which the calcium ions is dissolved and completely dissolved at normal temperature, thereby removing bubbles in a solution.

The above solution without the bubbles is coated on a desired target substrate by drop or spin coating to form the film.

Further, a test example of adhesive property, which is one of the properties of the film is as follows.

The typical test example of the adhesive property may include a peeling test. The peeling test is a test for measuring adhesive property in a vertical direction between the target material and the film. In this case, the peeling test is divided into a 90° peeling test while maintaining a peeling angle between the target material and the film at 90°, and a 180° peeling test while maintaining a peeling angle at 180°.

Figure 2A:
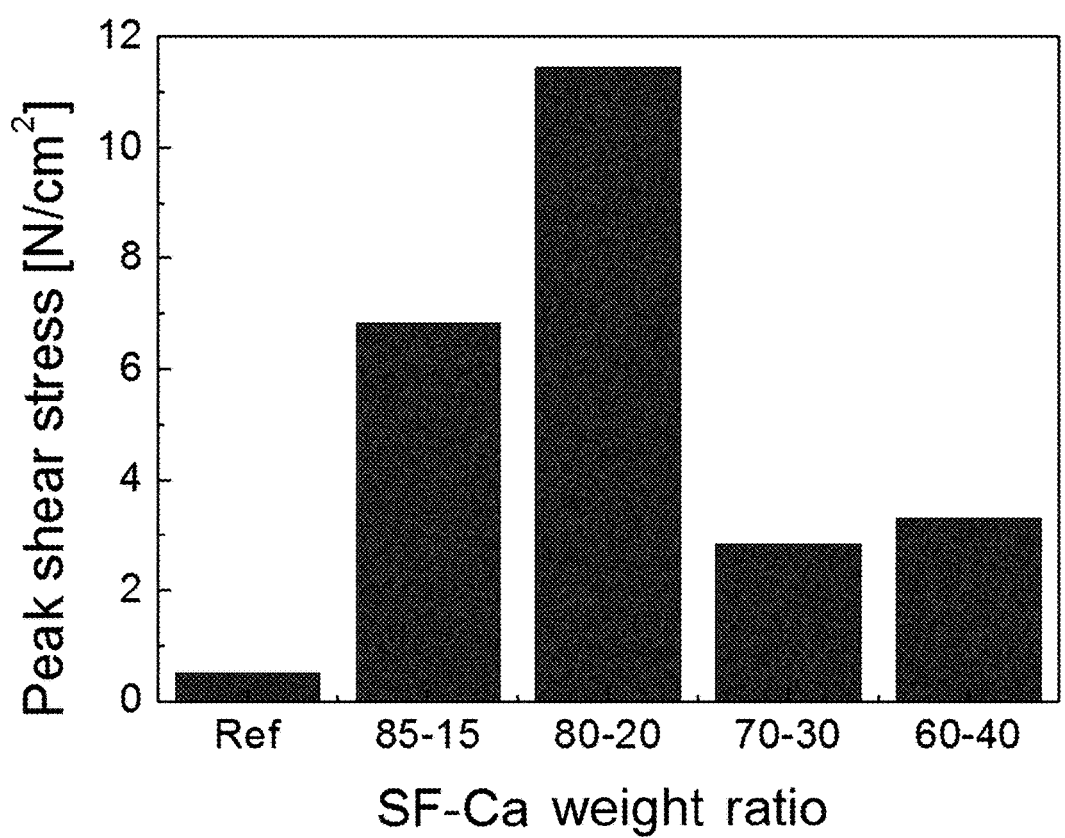
FIG. 2A illustrates a change in adhesive property with respect to a silk fibroin-calcium compound weight ratio at normal temperature and appropriate humidity.

FIG. 2A illustrates the change in adhesive property with respect to a silk fibroin and calcium compound weight ratio at normal temperature.

Figure 2B:
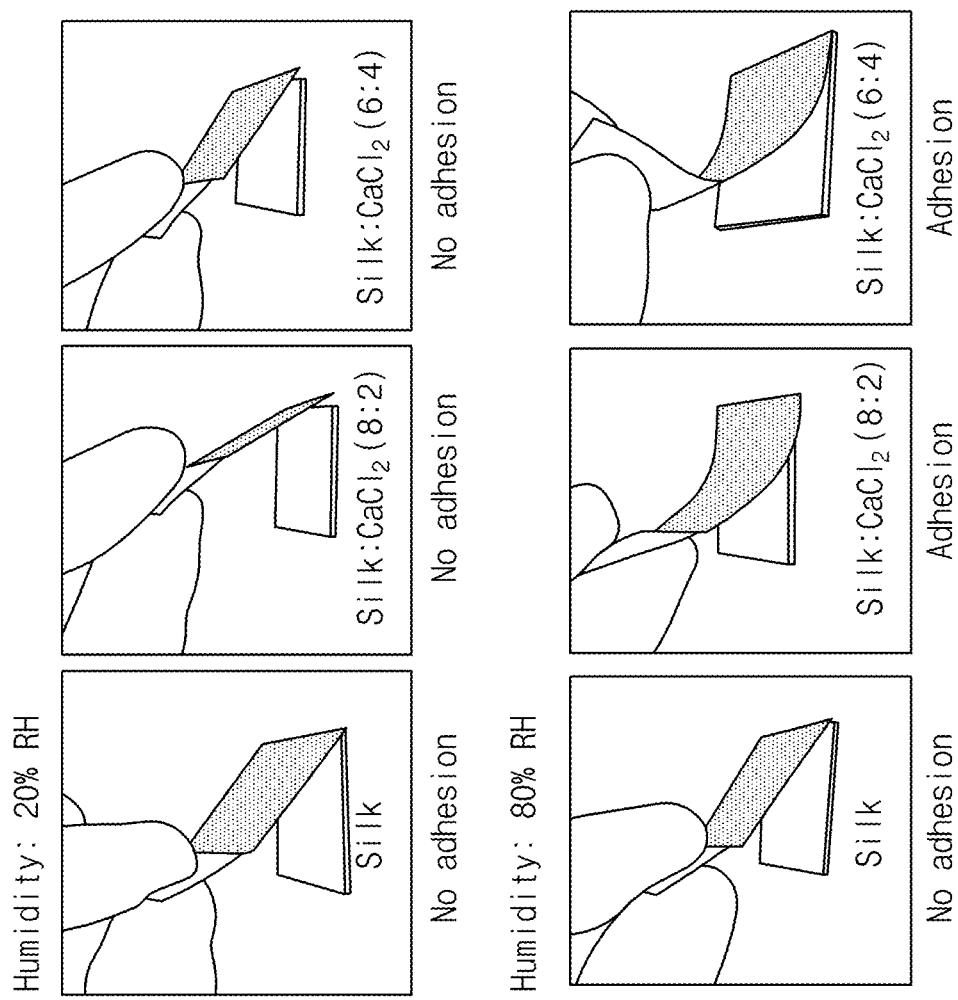
FIG. 2B is a diagram illustrating an example of a test result of a change in adhesive property with respect to a change in humidity of the silk fibroin and calcium compound at normal temperature and a specific weight ratio according to the humidity change.

As illustrated in FIG. 2B, each part of the contacted film and the target material is engaged with a jig, respectively, and pulled in a vertical direction at a constant speed (generally 100 mm/s in case of peeling test) to measure the peeling property.

In addition, FIG. 2B is a diagram illustrating an example of a test result of a change in adhesive property with respect to a change in humidity of silk fibroin-calcium compound at normal temperature and a specific weight ratio according to the humidity change. Referring to the test result of FIG. 2B, it can be seen that the higher the humidity of the silk fibroin and the calcium compound, the stronger the adhesive property.

Figure 2C:
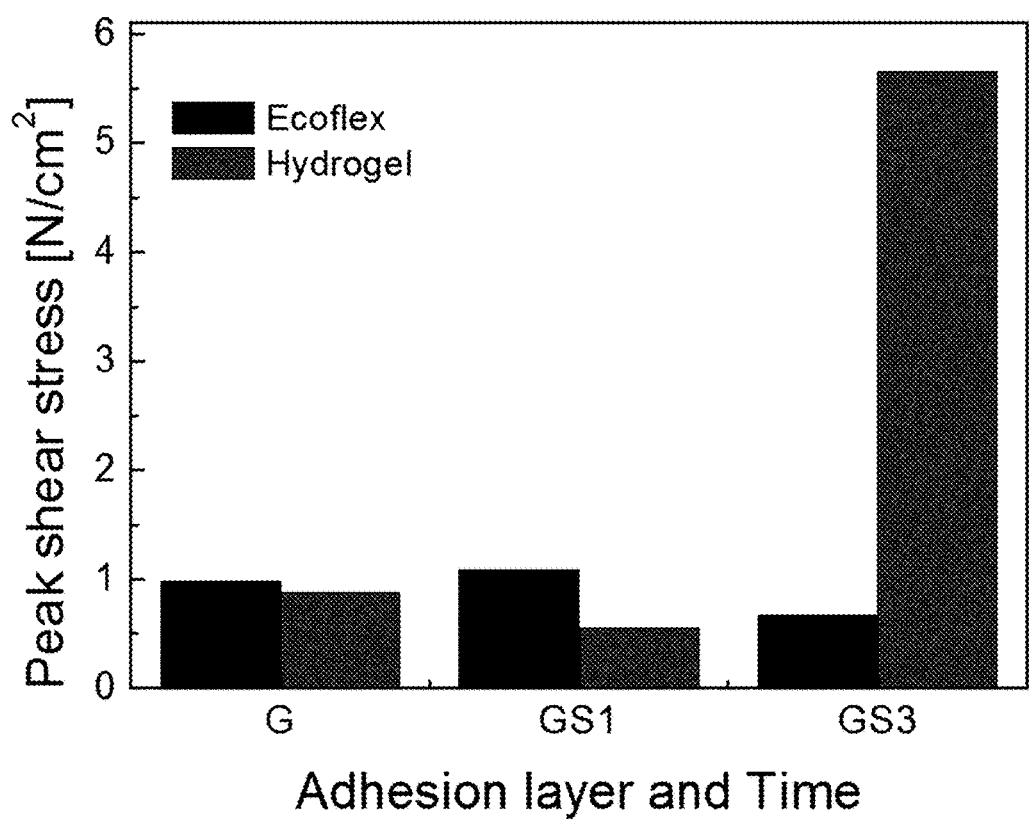
FIG. 2C is a diagram illustrating an example of a test result of measuring a change in adhesive property with respect to a target material (hydrophilic, hydrophobic material, etc.) contacting the silk fibroin and the calcium compound having a specific weight ratio at normal temperature and appropriate humidity.

FIG. 2C is a diagram illustrating an example of a test result of measuring a change in adhesive property with respect to a target material (hydrophilic, hydrophobic material, etc.) contacting the silk fibroin and the calcium compound having a specific weight ratio at normal temperature and appropriate humidity.

Figure 2D:
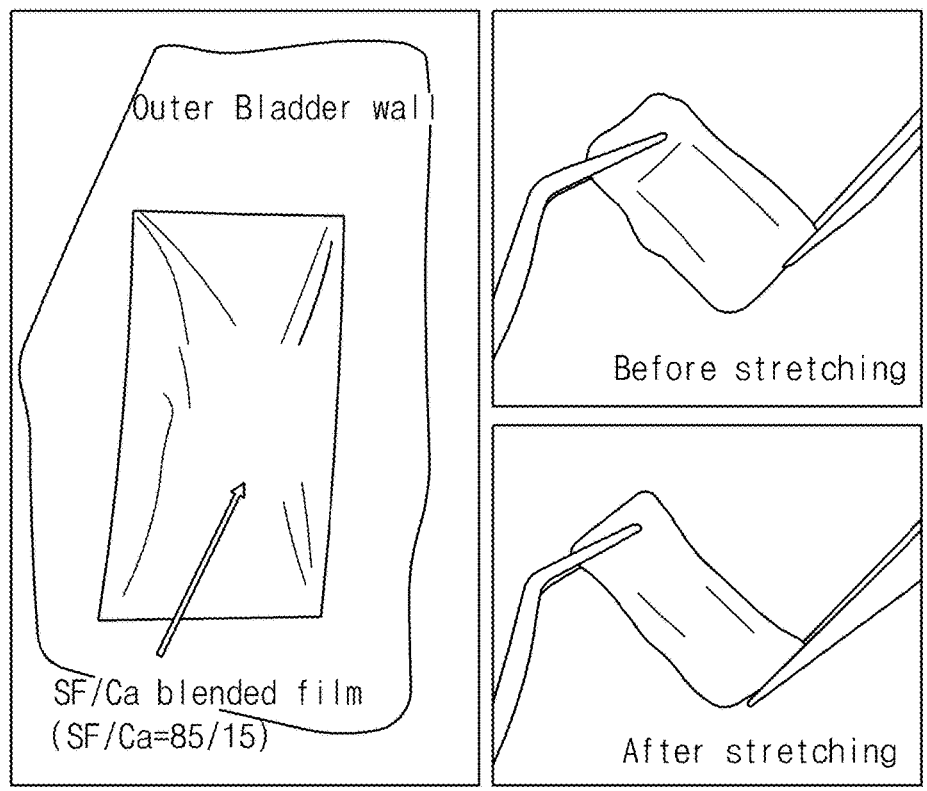
FIG. 2D is a diagram illustrating a test example of measuring adhesive property with respect to a horizontal direction between the target material and a film.

As illustrated FIG. 2D, a shear contact test is a test for measuring adhesive property with respect to a horizontal direction between the target material and the film. Each part of the contacted film and the target material is engaged with the jig and pulled in a horizontal direction at a constant speed (typically, 100 mm/s in case of the shear contact test) to measure shear contact property.

Figure 3:
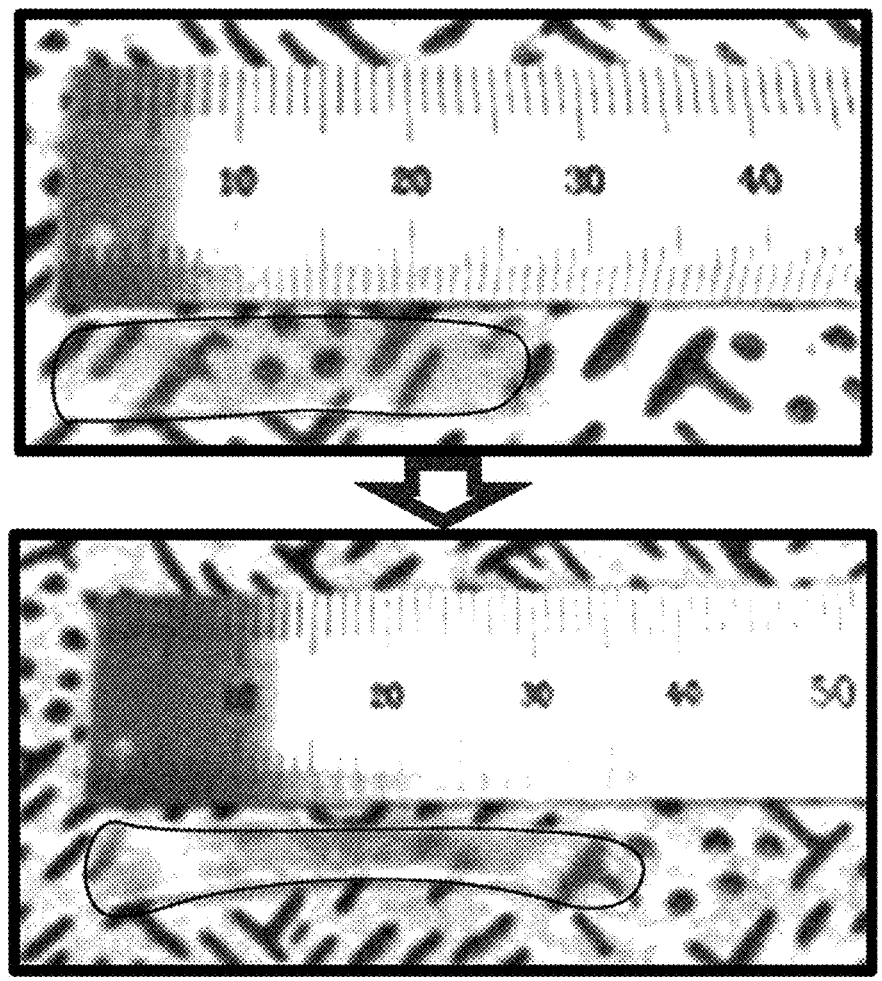
FIG. 3 is a diagram illustrating a test example of stretchability which is one of the properties of the film.

In addition, FIG. 3 illustrates a test example of stretchability which is one of the properties of the film.

The stretchability of the film is closely related to mechanical properties of the film material. The test example measuring the mechanical properties of the film materials may generally include a test using tensile tester equipment.

The tensile test equipment engages the film having a specific size with both ends of the jig and measures a change in force in response to a strain while applying a tensile or compressive stress at a constant speed (typically, 50 mm/s in case of a tensile test) at both ends of the jig, thereby analyzing tensile, compressive, fracture properties, or the like of the film. In addition, fatigue characteristics of the film are analyzed by a repeated stretching test at a specific strain.

For example, there is a test to measure the tensile, compressive and fracture properties with respect to the silk fibroin and calcium compound weight ratio at the normal temperature and appropriate humidity.

Figure 4:
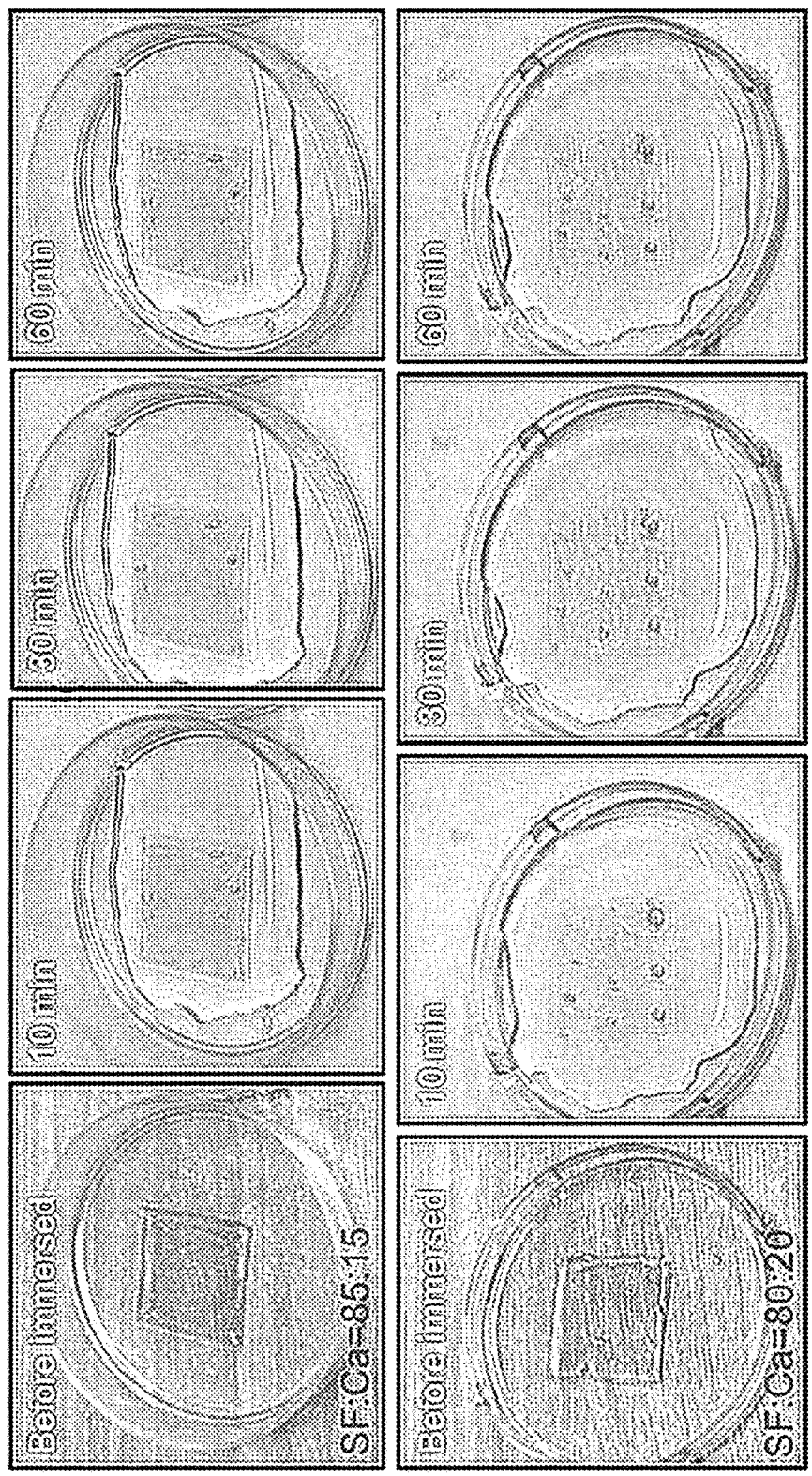
FIG. 4 is a diagram illustrating a test example of biodegradability which is one of properties of the film.

Further, FIG. 4 illustrates a test example of biodegradability which is one of the properties of the film.

If the film is inserted into a body like a bladder, a biodegradation process of decomposing the film by enzymes, humidity, temperature, PH, microorganisms or the like existing in the body is generated. In general, as the test method on the biodegradability measurement, there are a method for measuring biodegradability with enzymes which simulates a state of a body, humidity (80% or more), temperature (37° C.), and PH (3 to 4 in case of a bladder), outside the body and a method for measuring it by actually inserting the film into the body.

A weight of the film lost over time is measured by putting a film having a specific area into glass or Teflon beaker containing distilled water or enzymes and putting it in a constant temperature and humidity chamber simulating the temperature (37° C.) and humidity (80% or more) in a body.

FIG. 4 illustrates an example of the test result of measuring the silk fibroin and calcium compound weight ratio contained in the distilled water within the constant temperature and humidity chamber simulating temperature (37° C.), humidity (80% or more), and PH (3 to 4 in case of a bladder) in a body and the weight of the film lost over time.

Further, as another test example of biodegradability, there may be a test of measuring presence or absence of enzymes, a kind of enzymes, the weight of the lost film in the silk fibroin and the calcium compound having the specific weight ratio within the constant temperature and humidity chamber simulating the temperature (37° C.), humidity (80% or more) and PH (3 to 4 in case of a bladder).

As another test example of the biodegradability, there may be a test of measuring the weight of the film lost over the inserted time after the insertion of the film of the silk fibroin and the calcium compound having the specific weight ratio into an animal body (mouse, rabbit, monkey, etc.) by a surgical operation.

Figure 5:
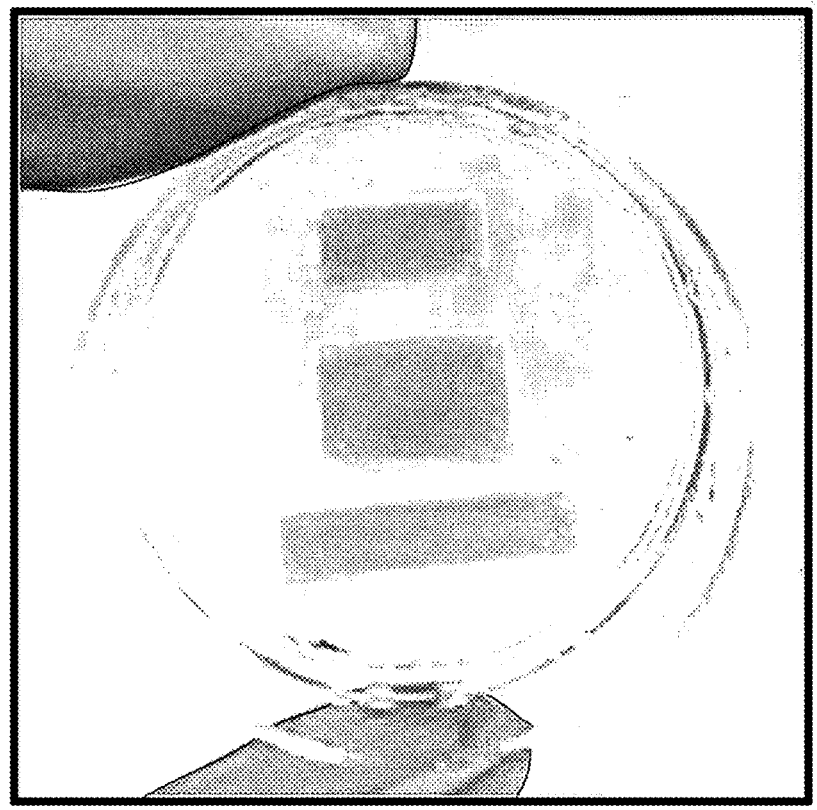
FIG. 5 is a diagram illustrating a test example of patternable possibility which is one of the properties of the film.

In addition, FIG. 5 is a diagram illustrating a test example of patternable possibility which is one of the properties of the film.

An etching process is essential for a patterning process represented by photolithography. Types of etching processes are divided into wet etching and dry etching. The wet etching is a process of etching a photo resist or an exposed target film using an etching solution, and the dry etching is a process of etching a target film exposed in a vacuum state using plasma. At this time, there is a method of examining the patternable possibility by analyzing the etching solution, an organic solvent used for cleaning the etching solution, or an influence by plasma according to the process method.

A change in characteristics such as a surface and a structure over time is analyzed by putting the film having a specific area in the glass or Teflon beaker containing the etching solution or the organic solvent.

In addition, as a test example of the patternable possibility, there may be a test of measuring surface characteristics changed depending on a kind of etching solutions (AZ 300 MIF, or the like) or organic solvents (acetone, distilled water, methanol, etc.) and the silk fibroin and calcium compound weight ratio over time by an optical microscope.

In addition, as the test example of the patternable possibility, there may be a test to analyze the structural characteristics (change in crystallinity, etc.) changed depending on the kind of etching solution or organic solvent and the silk fibroin-calcium compound weight ratio by using an infrared ray or a Raman spectroscopic analyzer.

Figure 6:
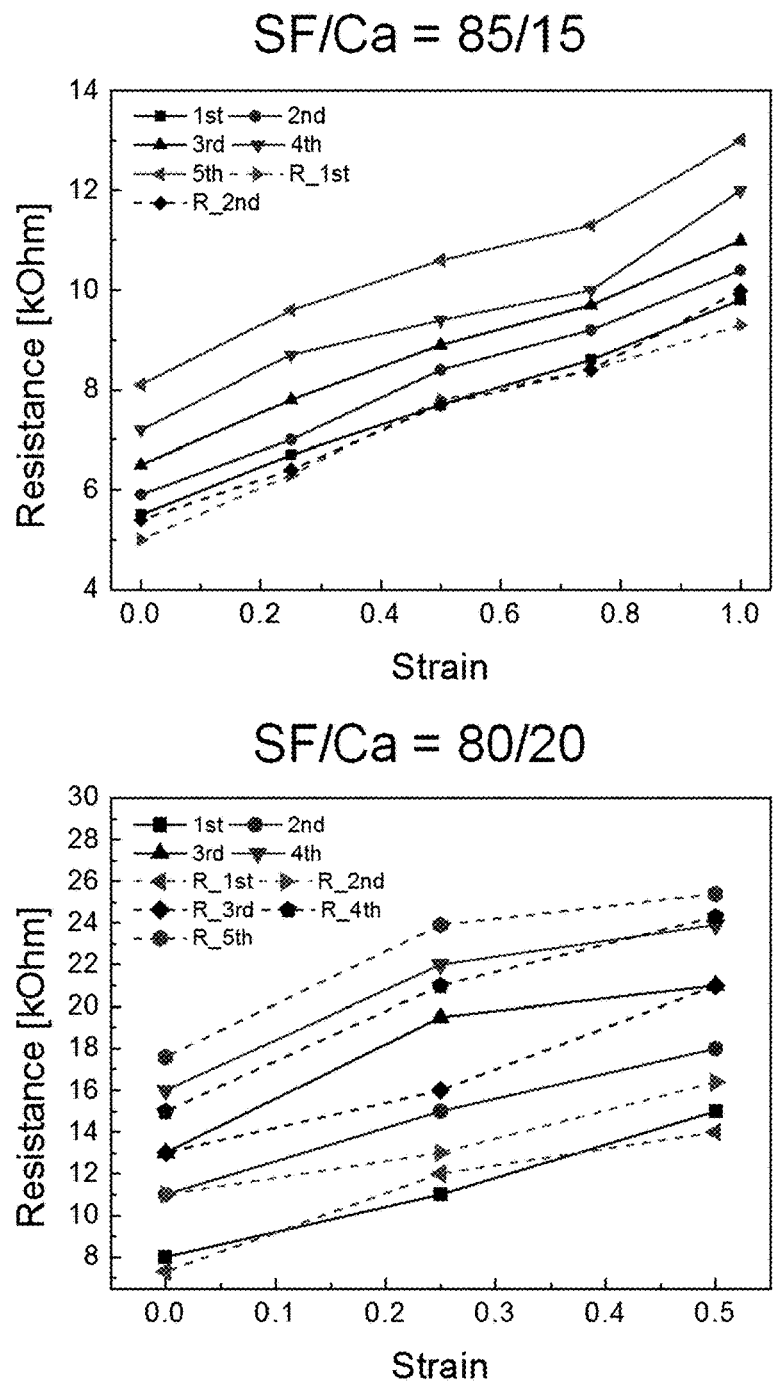
FIG. 6 is a diagram illustrating an example of a test result of conductivity which is one of the properties of the film.

In addition, FIG. 6 illustrates a test example of conductivity which is one of the properties of the film.

The film needs to have conductivity in order to derive a volume changed in response to the expansion or contraction of the bladder by using a change in electric capacity, a change in resistance, and the like.

As a method for measuring the conductivity of the film, there is a method for using an RLC meter. The conductivity is measured by contacting two electric wires connected to the RLC meter to both ends of the film at specific intervals by silver paste or carbon paste.

In addition, as the test example of conductivity, there may be a test of measuring a change in conductivity in response to the silk fibroin and calcium compound weight ratio at normal temperature and appropriate humidity by the RLS meter.

In addition, as the test example of conductivity, there may be a test of measuring a change in conductivity in response to the humidity of the silk fibroin and the calcium compound having a specific weight ratio at normal temperature by the RLC meter.

In addition, FIG. 6 illustrates a test result of measuring the change in conductivity in response to the strain of the silk fibroin and the calcium based compound having the specific weight ratio at normal temperature and appropriate humidity by the RLC meter, as the example of the test result of the conductivity.

Figure 7A:
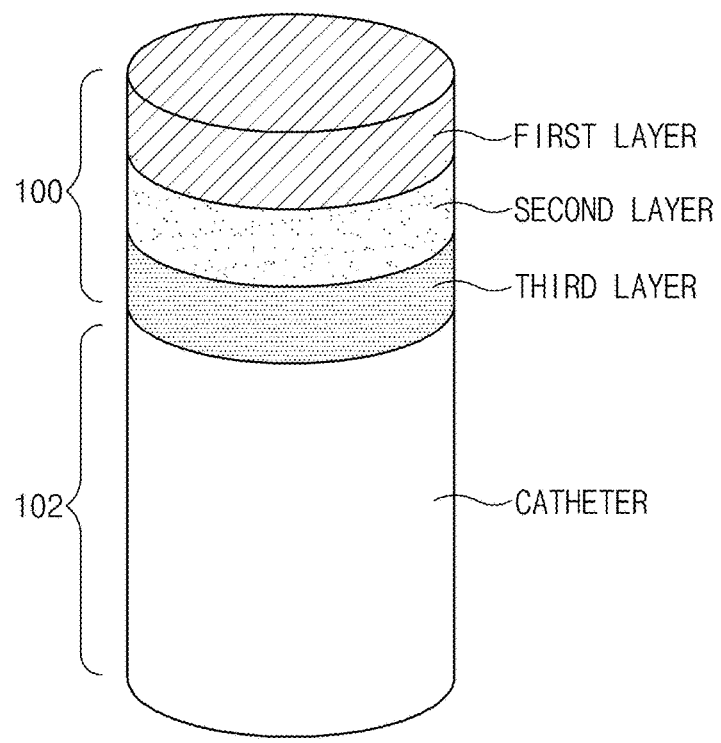
FIG. 7A is a diagram illustrating a structure of a sensor 100 according to an exemplary embodiment of the present embodiment.

FIG. 7A is a diagram illustrating a structure of a sensor 100 according to an exemplary embodiment of the present embodiment.

The sensor 100 is configured of films of first to third layers. Each film is made of the silk fibroin and the calcium compound as described above. In addition, each film has adhesive property, stretchability, biodegradability, conductivity, and patternable possibility.

The first layer has a first surface attached to viscera and a second surface opposite to the first surface. Further, the first layer is made of the silk fibroin and the calcium compound having a weight ratio ranging from about 80:20 to 85:15. Thus, the biodegradability of the first layer is maintained for about 20 hours. In addition, the first layer has stretchability, and therefore is expanded and contracted as the viscera is expanded or contracted.

Figure 7B:
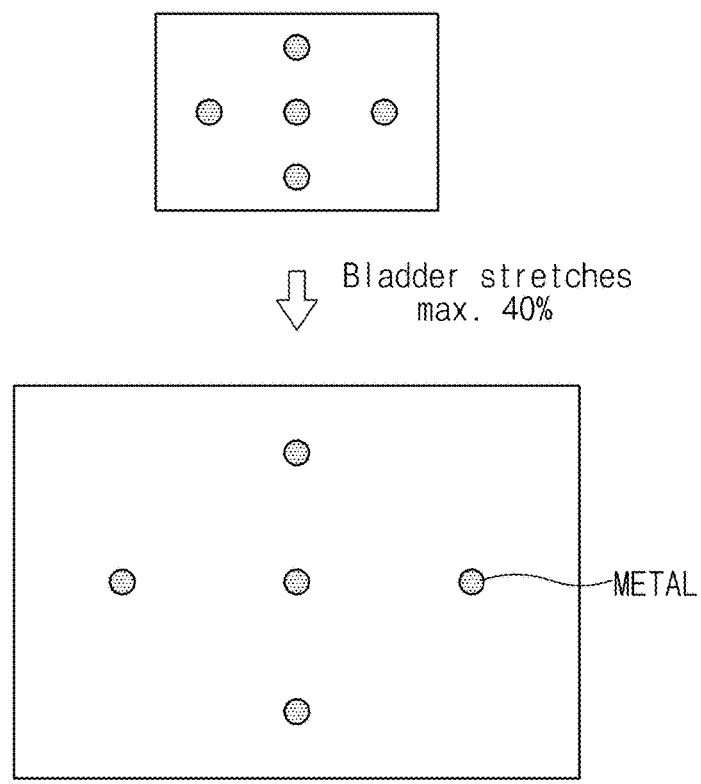
FIG. 7B is a diagram illustrating a change in a marker inserted into a second layer.

The second layer has a third surface attached to the second surface and a fourth surface opposite to the third surface. In addition, the second layer has stretchability, and therefore is expanded and contracted as the viscera is expanded or contracted. Further, the second layer is made of the silk fibroin and the calcium compound having a weight ratio ranging from about 80:20 to 85:15. Further, referring to FIG. 7B of the present application, the second layer includes a marker made of at least two or more metals. The metal may be, for example, gold that is harmless to a human body and may be discharged. If the second layer is expanded or contracted as the viscera is expanded or contracted, the position of the metal contained in the second layer is also changed correspondingly. As the position of the metal is changed, a signal reflected by the metal and transmitted outside a body is changed. It is possible to detect that the position of the metal is changed in response to the change in the signal. Here, the signal may be, for example, an ultrasonic wave or an electromagnetic wave. It is possible to measure how much the second layer is expanded or contracted using the detected displacement of the metal and how much the viscera is expanded or contracted based on how much the second layer is expanded or contracted. It is possible to measure viscera compliance by measuring how the viscera is expanded or contracted.

The third layer has a fifth surface attached to the fourth surface and a sixth surface opposite to the fifth surface and attached to a catheter. Further, the third layer has biodegradability. A duration of the biodegradability of the third layer may be controlled depending on the ratio of the silk fibroin to the calcium compound. The duration of the biodegradability of the third layer is shorter than that of the first layer.

For example, the silk fibroin and the calcium compound of the third layer have a weight ratio ranging from about 70:30 to 60:40. Thus, the biodegradability of the first layer is maintained for about 30 minutes. Further, the third layer has adhesive property. Thus, the third layer may be attached to the catheter until it is biodegraded.

Figure 7C:
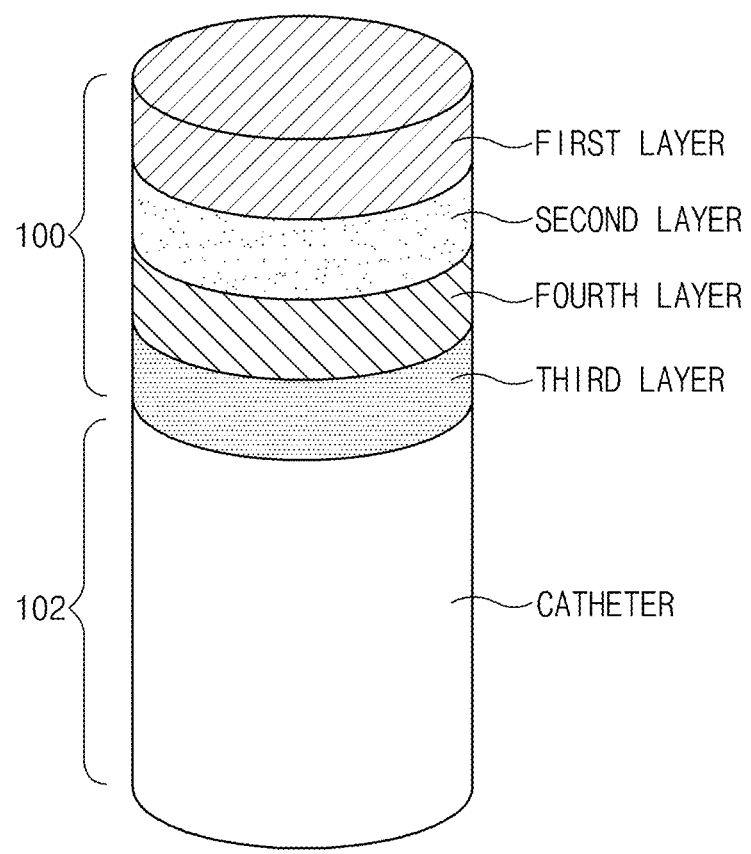
FIG. 7C is a diagram illustrating a structure of a sensor 100 according to another exemplary embodiment of the present embodiment.

FIG. 7C is a diagram illustrating a structure of a sensor 100 according to another exemplary embodiment of the present embodiment.

The sensor 100 is configured of a film of first to fourth layers. Each film is made of the silk fibroin and the calcium compound as described above. In addition, each film has adhesive property, stretchability, biodegradability, conductivity, and patternable possibility.

The first layer has a first surface attached to viscera and a second surface opposite to the first surface. Further, the first layer is made of the silk fibroin and the calcium compound having a weight ratio ranging from about 80:20 to 85:15. Thus, the biodegradability of the first layer is maintained for about 20 hours. In addition, the first layer has stretchability, and therefore is expanded and contracted as the viscera is expanded or contracted.

The second layer has a third surface attached to the second surface and a fourth surface opposite to the third surface. In addition, the second layer has stretchability, and therefore is expanded and contracted as the viscera is expanded or contracted. Further, a resistance value is changed as the second layer is expanded or contracted. For example, FIG. 6 illustrates the resistance value changed depending on how much it is expanded or contracted when the ratio of the silk fibroin and the calcium compound is 85:15 or 80:20.

The fourth layer has a fifth surface attached to the fourth surface and a sixth surface opposite to the fifth surface. The fourth layer includes a circuit capable of measuring the resistance value of the second layer and transmitting the measured resistance value to the outside. In addition, the circuit is turned on by acquiring externally generated vibration energy (e.g., by receiving ultrasonic waves) including PZT. In addition, since the circuit is a circuit in which each element is embedded in the film of the present disclosure, when the film is biodegraded, the circuit is decomposed so that each element may be discharged to the outside of the body. In addition, any circuit may be applied as long as the circuit of the fourth layer measures the resistance value of the second layer and transmits the measured resistance value to the outside.

The third layer has a seventh surface attached to the sixth surface and an eighth surface opposite to the seventh surface and attached to the catheter. Further, the third layer has biodegradability. The duration of the biodegradability of the third layer may be controlled depending on the ratio of the silk fibroin to the calcium compound. The duration of the biodegradability of the third layer is shorter than that of the first layer. For example, the silk fibroin and the calcium compound of the third layer have a weight ratio ranging from about 60:40 to 70:30. Thus, the biodegradability of the third layer is maintained for about 30 minutes. Further, the third layer has adhesive property. Thus, the third layer may be attached to the catheter before it is biodegraded.

Figure 7D:
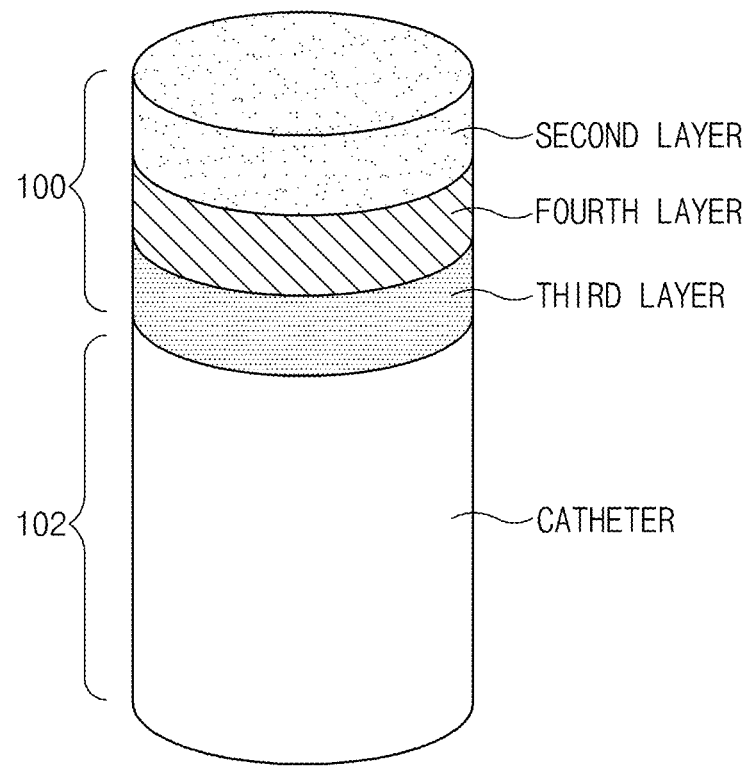
FIG. 7D is a diagram illustrating the structure of the sensor 100 according to another exemplary embodiment of the present embodiment.

FIG. 7D is a diagram illustrating the structure of the sensor 100 according to another exemplary embodiment of the present embodiment.

The sensor is configured of a film of the second, fourth and third layers. Each film is made of the silk fibroin and the calcium compound as described above. In addition, each film has adhesive property, stretchability, biodegradability, conductivity, and patternable possibility.

The second layer has the first surface attached to viscera and the second surface opposite to the first surface. Further, the second layer is made of the silk fibroin and the calcium compound having a weight ratio ranging from about 80:20 to 85:15. Thus, the biodegradability of the second layer is maintained for about 20 hours. In addition, the second layer has stretchability, and therefore is expanded and contracted as the viscera is expanded or contracted. Further, a resistance value is changed as the second layer is expanded or contracted.

The fourth layer has the third surface attached to the second surface and the fourth surface opposite to the third surface. The fourth layer includes a circuit capable of measuring the resistance value of the second layer and transmitting the measured resistance value to the outside. Further, the circuit is turned on by acquiring externally generated vibration energy including PZT. In addition, since the circuit is a circuit in which each element is embedded in the film of the present disclosure, when the film is biodegraded, the circuit is decomposed so that each element may be discharged to the outside of the body. In addition, any circuit may be applied as long as the circuit of the fourth layer measures the resistance value of the second layer and transmits the measured resistance value to the outside.

The third layer has the fifth surface attached to the fourth surface and the sixth surface opposite to the fifth surface and attached to the catheter. Further, the third layer has biodegradability. The duration of the biodegradability of the third layer may be controlled depending on the ratio of the silk fibroin to the calcium compound. The duration of the biodegradability of the third layer is shorter than that of the second layer. For example, the silk fibroin and the calcium compound of the third layer have a weight ratio ranging from about 60:40 to 70:30. Thus, the biodegradability of the third layer is maintained for about 30 minutes. Further, the third layer has adhesive property. Thus, the third layer may be attached to the catheter before it is biodegraded.

Figure 8:
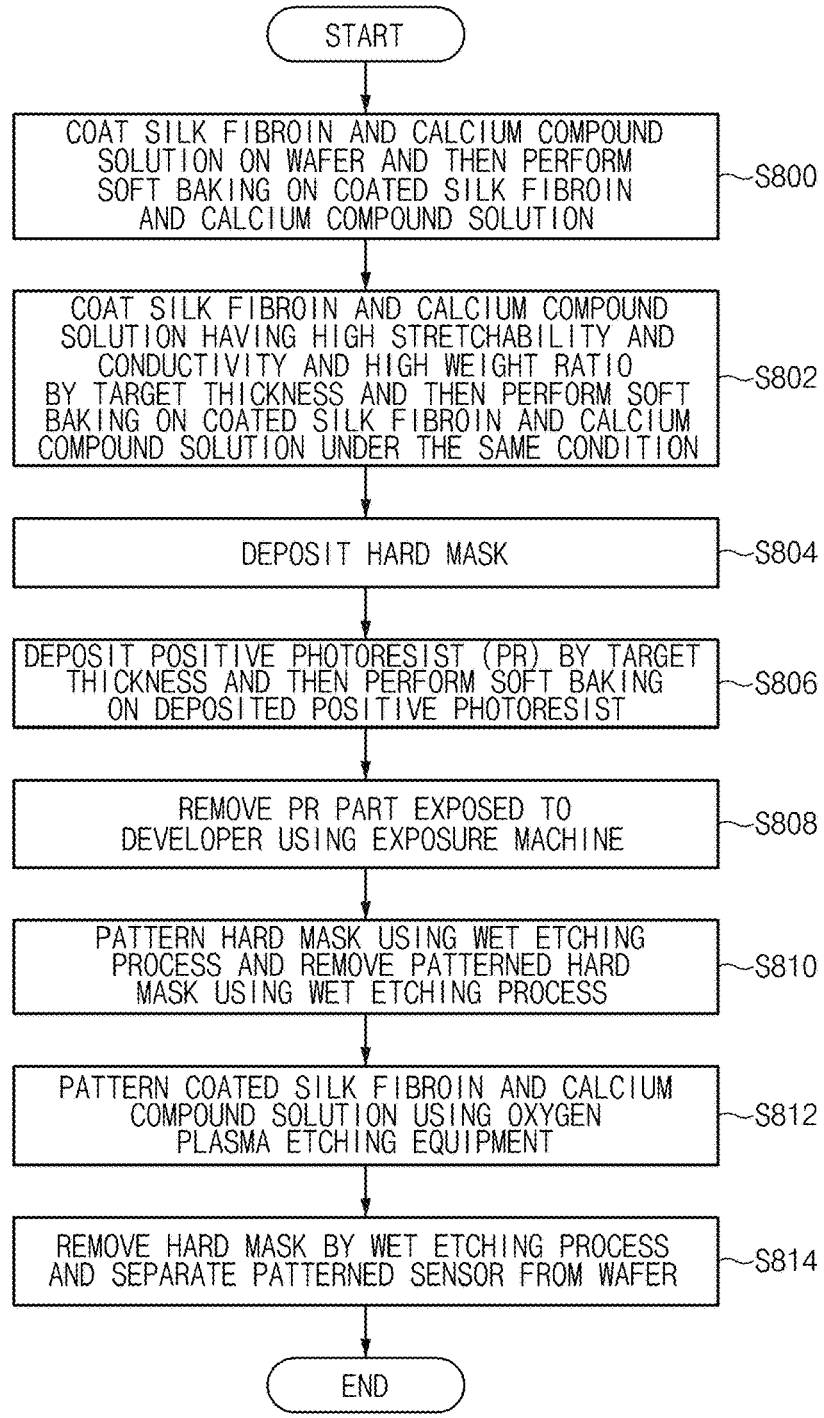
FIG. 8 is a diagram illustrating a method for manufacturing a sensor 100.

FIG. 8 is a diagram illustrating a method for manufacturing a sensor 100. The method of manufacturing a sensor 100 according to an exemplary embodiment of the present disclosure is as follows.

The silk fibroin and the calcium compound solution having high adhesive property, slightly low biodegradability, and a specific weight ratio are coated on a wafer by a target thickness using a spin coater and then suffer from soft baking at 75° C. for 10 minutes (S800).

Thereafter, the silk fibroin and the calcium compound solution having the stretchablilty, the conductivity, and the high weight ratio are coated by a target thickness using the spin coater and then suffer from the soft baking under the same conditions (S802).

Thereafter, a hard mask is deposited using physical vapor deposition (S804).

Thereafter, a positive photo resist is deposited by a target thickness using the spin coater, suffers from the soft baking at 110° C. for 3 minutes (S806), is exposed by an exposure machine, and then the PR part exposed to a developer is removed (S808).

Thereafter, the hard mask is patterned by a wet etching process and the remaining PR part is removed by an asher (S810).

Thereafter, the film of the coated silk fibroin and calcium compound is patterned using by oxygen plasma etching equipment (S812).

Thereafter, the hard mask is removed by the wet etching process and the patterned sensor is separated from the wafer to complete the sensor manufacturing process (S814).

Figure 9:
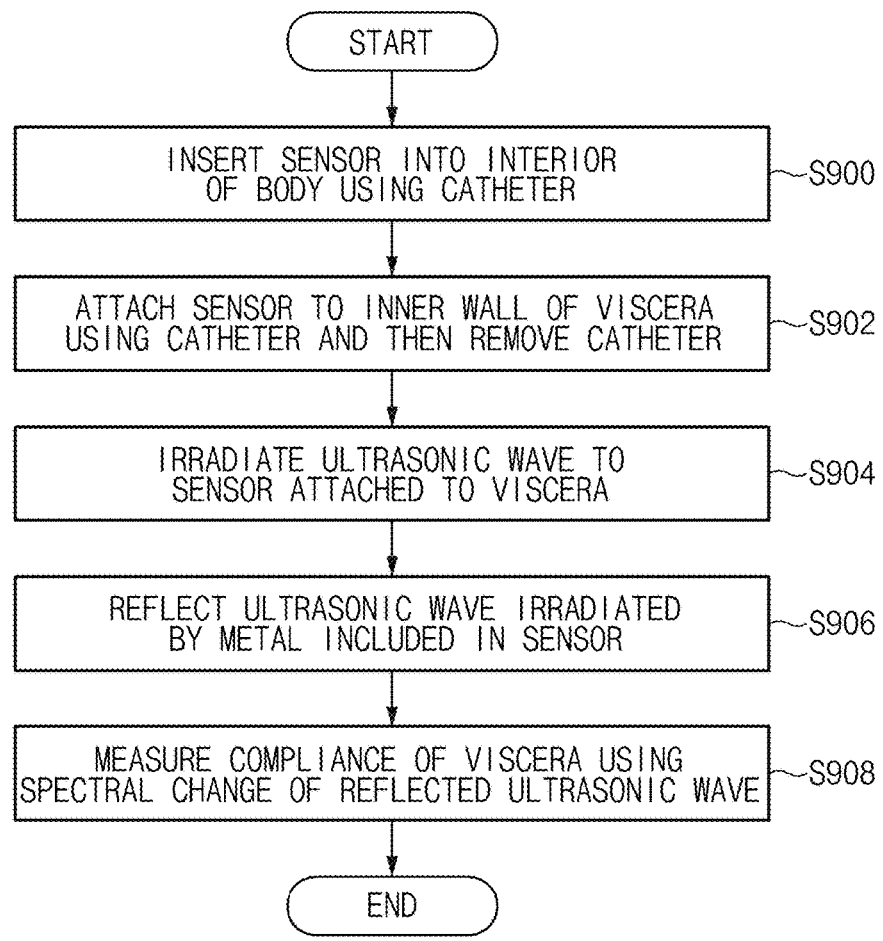
FIG. 9 is a flow chart illustrating a method for measuring viscera compliance using the sensor 100 according to an exemplary embodiment of the present disclosure.

FIG. 9 is a flow chart illustrating a method for measuring viscera compliance using the sensor 100 according to an exemplary embodiment of the present disclosure.

The sensor 100 according to the exemplary embodiment of the present disclosure is the sensor illustrated in FIG. 7A. That is, the sensor 100 according to the exemplary embodiment of the present disclosure is configured of a film of the first to third layers. The first layer is made of the silk fibroin and the calcium compound having a weight ratio ranging from about 80:20 to 85:15. Thus, the biodegradability of the first layer is maintained for about 20 hours. In addition, the first layer has stretchability, and therefore is expanded and contracted as the viscera is expanded or contracted.

The second layer is expanded or contracted as the viscera is expanded or contracted. Further, the second layer is made of the silk fibroin and the calcium compound having a weight ratio ranging from about 80:20 to 85:15. In addition, the second layer includes a marker made of at least two metals. In addition, the metal contained in the second layer may be positioned at an edge part of the second layer. The metal may be, for example, gold that is harmless to a human body and may be discharged. If the second layer is expanded or contracted as the viscera is expanded or contracted, the position of the metal contained in the second layer is also changed correspondingly. As the position of the metal is changed, a signal reflected by the metal and transmitted outside a body is changed. It is possible to detect that the position of the metal is changed in response to the change in the signal. Here, the signal may be, for example, an ultrasonic wave or an electromagnetic wave. It is possible to measure how much the second layer is expanded or contracted using the detected displacement of the metal and how much the viscera is expanded or contracted based on how much the second layer is expanded or contracted. It is possible to measure viscera compliance by measuring how much the viscera is expanded or contracted.

The third layer has biodegradability. The duration of the biodegradability of the third layer may be controlled depending on the ratio of the silk fibroin to the calcium compound. The duration of the biodegradability of the third layer is shorter than that of the first layer. For example, the silk fibroin and the calcium compound of the third layer have a weight ratio ranging from about 60:40 to 70:30. Thus, the biodegradability of the third layer is maintained for about 30 minutes. Further, the third layer has adhesive property. Thus, the third layer may be attached to the catheter until it is biodegraded.

The sensor 100 according to the exemplary embodiment of the present disclosure described above is attached to the end of the catheter to be inserted into an interior of the body (S900). If the first surface of the sensor 100 is attached to the viscera and the third layer is biodegraded, the catheter and sensor 100 are separated from each other and thus only the catheter is taken out of the body again (S902).

The ultrasonic wave is irradiated to the sensor 100 attached to an in-vivo apparatus from the outside of the body (S904). The ultrasonic wave irradiated to the sensor 100 may be reflected by the marker included in the sensor 100 and may receive the reflected ultrasonic wave (S906). The expansion or contraction of the viscera causes the expansion or contraction of the sensor 100 attached to the viscera. In addition, the expansion or contraction of the sensor 100 causes the position movement of the marker included in the sensor 100. Accordingly, the viscera compliance is measured using the spectral change of the reflected wave of the ultrasonic wave irradiated by the marker moving by the expansion or contraction of the viscera (S908).

Figure 10:
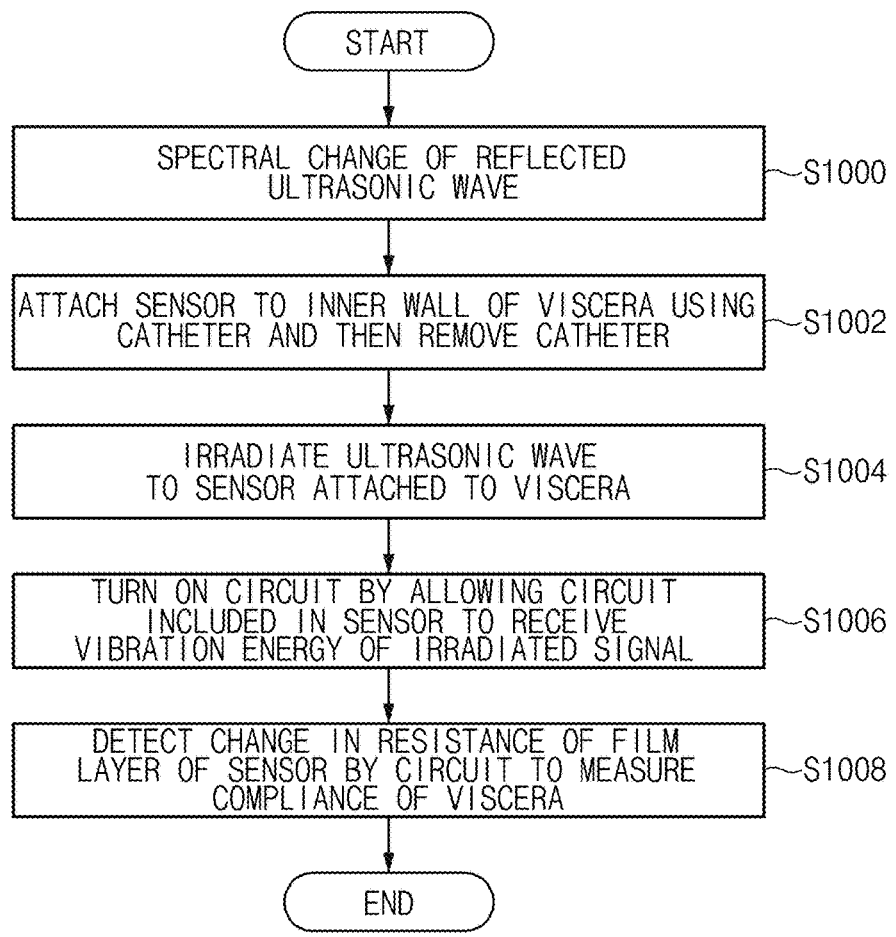
FIG. 10 is a flow chart illustrating a method for measuring viscera compliance using a sensor 100 according to another exemplary embodiment of the present disclosure.

FIG. 10 is a flow chart illustrating a method for measuring viscera compliance using a sensor 100 according to another exemplary embodiment of the present disclosure.

The sensor 100 according to another exemplary embodiment of the present disclosure is the sensor illustrated in FIG. 7C or 7D.

The sensor 100 is configured of a film of the first to fourth layers. The first layer has a surface attached to the viscera. The second layer has stretchability, and therefore is expanded or contracted as the viscera is expanded or contracted. Further, a resistance value is changed as the second layer is expanded or contracted. The fourth layer includes a circuit capable of measuring the resistance value of the second layer and transmitting the measured resistance value to the outside. In addition, the circuit included in the fourth layer is a circuit in which elements are embedded in the film, and therefore if the film is biodegraded, the circuit is biodegraded and the circuit is decomposed accordingly, such that each element may be discharged outside the body. The third layer has a surface that has biodegradability and is attached to the catheter. Further, the duration of the biodegradability of the third layer is shorter than that of the first layer.

Alternatively, the sensor 100 is configured of a film of the second, fourth, and third layers. The second layer has the surface that is attached to the viscera and stretchability, and therefore is expanded or contracted if the viscera is expanded or contracted. Further, a resistance value is changed as the second layer is expanded or contracted. The fourth layer includes a circuit capable of measuring the resistance value of the second layer and transmitting the measured resistance value to the outside. In addition, the circuit included in the fourth layer is a circuit in which elements are embedded in the film, and therefore if the film is biodegraded, the circuit is biodegraded and the circuit is decomposed accordingly, such that each element may be discharged outside the body. The third layer has a surface that has biodegradability and is attached to the catheter. Further, the duration of the biodegradability of the third layer is shorter than that of the second layer.

The corresponding sensor 100 is attached to the end of the catheter to be inserted into the interior of the body (S1000). If the first layer or the second layer of the sensor 100 is attached to the viscera and the third layer is biodegraded, the catheter and sensor 100 are separated from each other and thus only the catheter is taken out of the body again (S1002).

Figure 11:
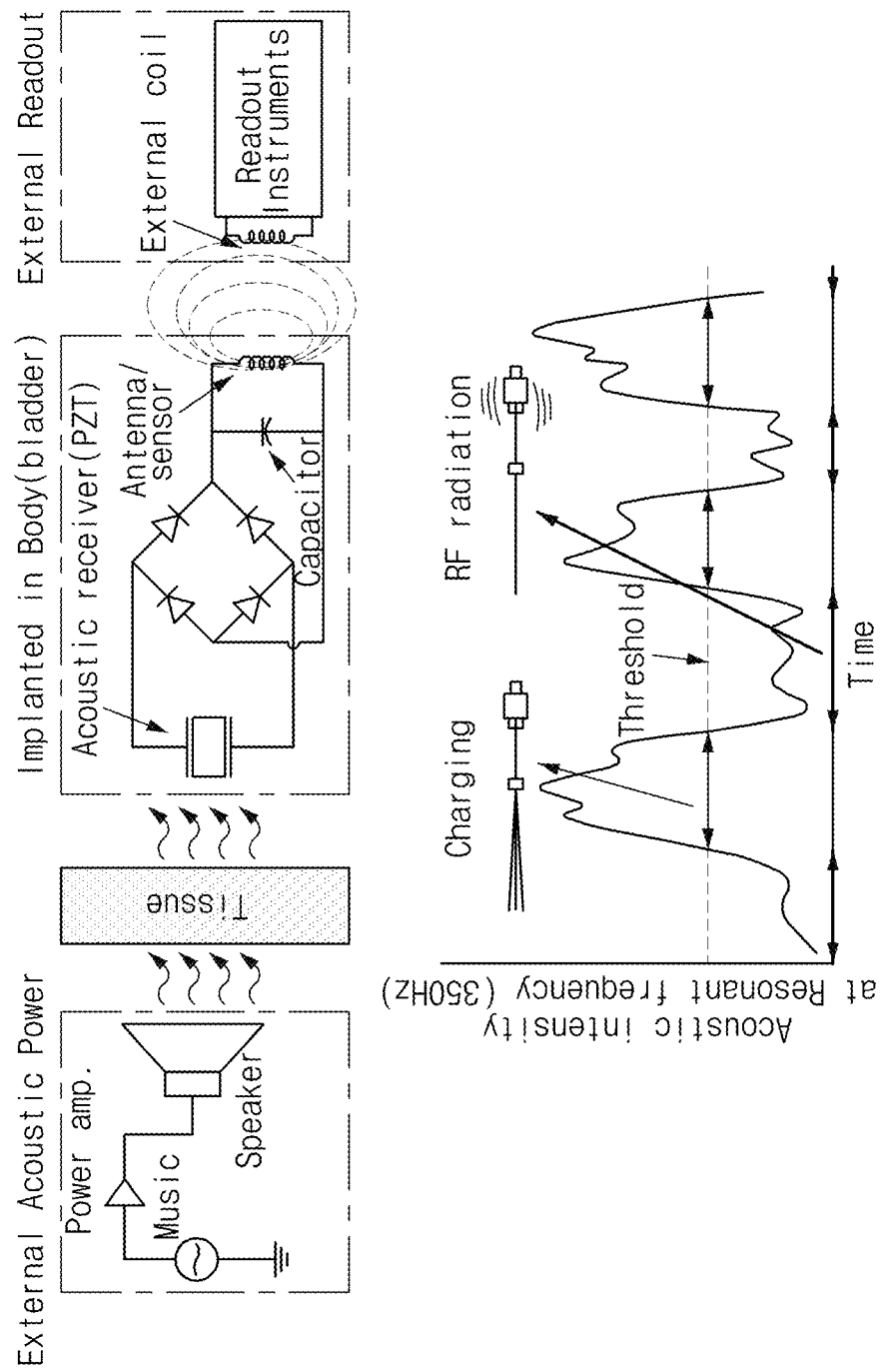
FIG. 11 is a diagram illustrating an exemplified circuit formed on a fourth layer.

Thereafter, the signal having vibration energy is irradiated to the sensor attached within the viscera (S1004). The irradiated signal is received by the circuit included in the fourth layer to turn on the circuit (S1006). The drawing of the exemplified circuit is illustrated in FIG. 11. However, the circuit used in the present disclosure is not limited to the circuit of FIG. 11, but the configuration thereof is not limited as long as it may perform the function of the fourth layer.

The circuit is turned on to measure the resistance value changed in response to the expansion or contraction of the second layer and transmit the measured resistance value to the outside (S1008). Alternatively, the circuit may be a circuit that can measure the resistance value from the outside without directly transmitting the resistance value to the outside.

Figure 12:
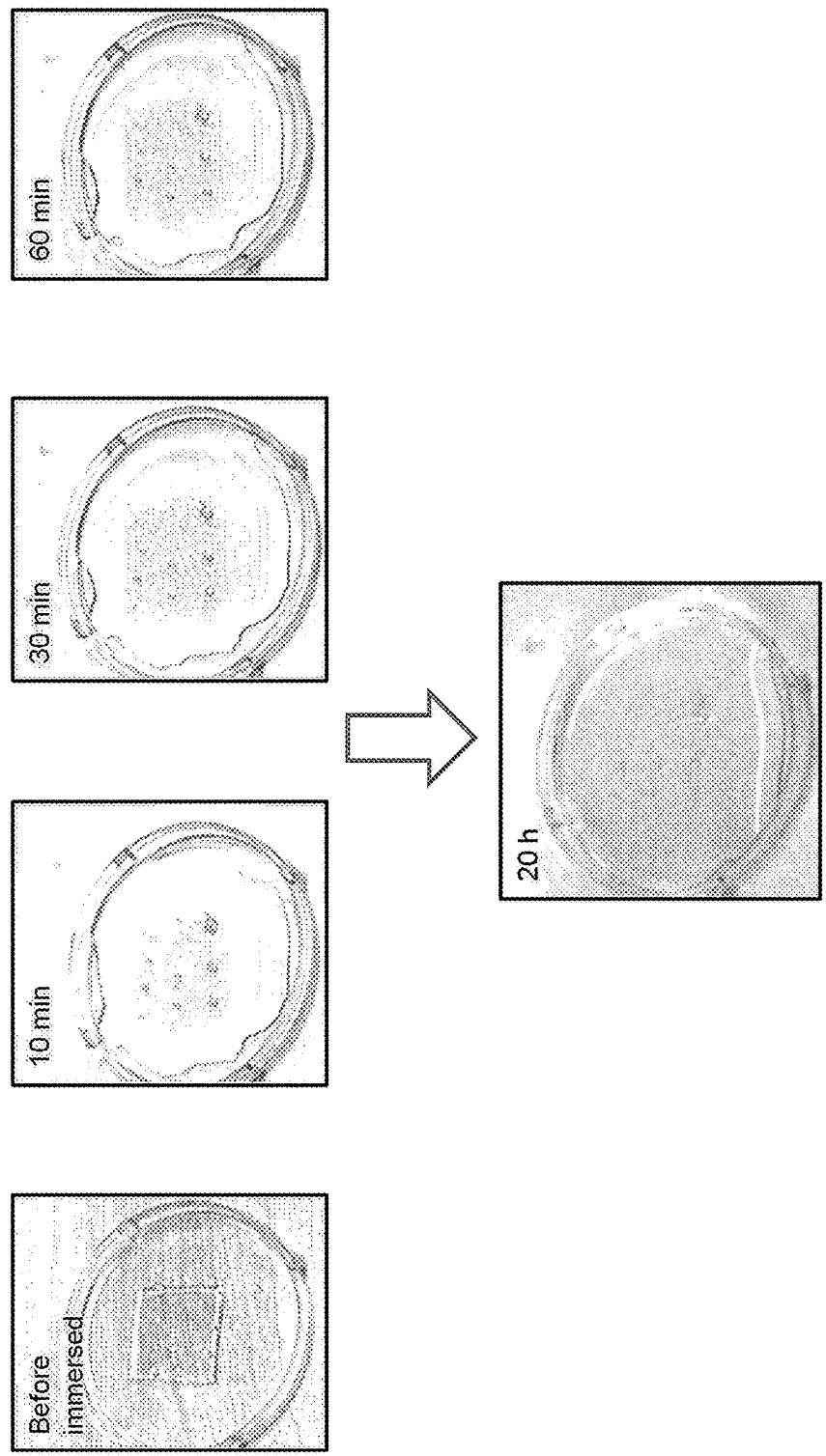
FIG. 12 is a diagram illustrating an example of a test result of biodegradability of a first layer, a second layer, and the fourth layer according to the exemplary embodiment of the present disclosure.

FIG. 12 is a diagram illustrating an example of a test result of biodegradability of a first layer, a second layer, and the fourth layer according to the exemplary embodiment of the present disclosure.

Figure 13:
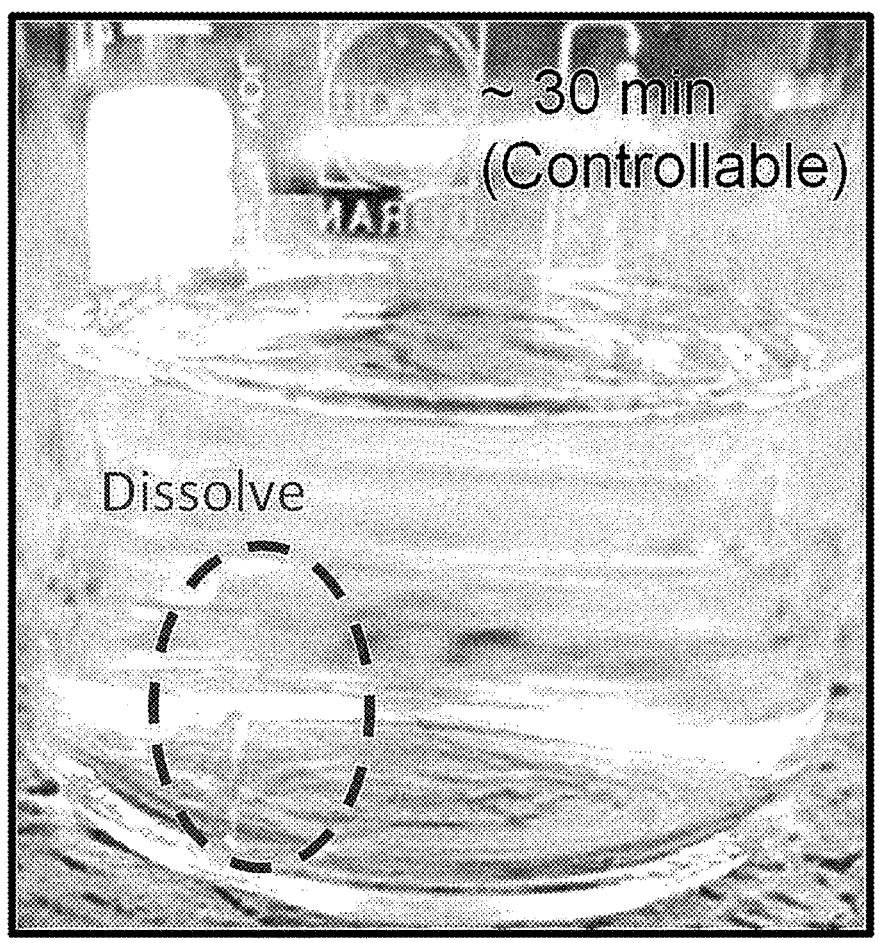
FIG. 13 is a diagram illustrating an example of the test result of the biodegradability of the third layer according to the exemplary embodiment of the present disclosure.

FIG. 13 is a diagram illustrating an example of the test result of the biodegradability of the third layer according to the exemplary embodiment of the present disclosure. If the weight ratio of the silk fibroin to the calcium compound is 60:40, it is the result example in which the third layer is completely dissolved in 30 minutes.

According to the exemplary embodiment of the present disclosure, it is possible to measure the viscera compliance without performing the surgical procedure by using the sensor that can be inserted into the viscera by the catheter.

In addition, according to the exemplary embodiment of the present disclosure, it is possible to measure the elements required to diagnose diseases while minimizing a patient's pain because the sensor can be removed without the surgical procedure by having the biodegradability.

The apparatus or system according to various embodiments may include at least one of the above-mentioned components, may not include some thereof, or may further include other additional components. The exemplary embodiments disclosed in the present document are presented for the purpose of explanation and understanding of the disclosed technical contents, and do not limit the scope of the present disclosure. Accordingly, the scope of the present document should be interpreted to include all modifications and or various other exemplary embodiments based on the technical idea of the present disclosure.

What is claimed is:

1. A sensor adapted to be attached to inner wall of viscera to measure a change in compliance of the viscera, comprising:
   a first layer having a first surface and a second surface opposite to the first surface;
   a second layer having a third surface attached to the second surface and a fourth surface opposite to the third surface and adapted to expand or contract as the viscera is expanded or contracted; and
   a third layer having a fifth surface attached to the fourth surface and a sixth surface opposite to the fifth surface and adapted to be attached to a catheter,
   wherein each of the first layer, the second layer, and the third layer includes a film including silk fibroin and a calcium compound,
     the sensor is adapted to be inserted into an interior of a body,
     the first surface is adapted to be attached to the inner wall of the viscera for maintaining the sensor in the viscera after the catheter is detached from the sensor and removed from the viscera,
     the second layer has a marker made of at least two metals and inserted into the film, and
     each metal of the at least two metals is inserted into a different edge part of the film.

2. The sensor of claim 1, wherein the film is patterned in various forms.

3. The sensor of claim 1, wherein the film has adhesive property of 11 N/cm$^2$ when a silk fibroin-calcium compound weight ratio is 80:20,
   adhesive property of 7 N/cm$^2$ when the silk fibroin-calcium compound weight ratio is 85:15, and
   adhesive property of 5 N/cm$^2$ when a silk fibroin-calcium compound weight ratio is 60:40.

4. The sensor of claim 2, wherein a biodegradable time of the film is adjusted depending on the silk fibroin-calcium compound weight ratio.

5. The sensor of claim 1, wherein a resistance value of the film is adjusted depending on the silk fibroin-calcium compound weight ratio.

6. The sensor of claim 4, wherein the silk fibroin-calcium compound weight ratio ranges from 80:20 to 85:15.

7. The sensor of claim 4, wherein the silk fibroin-calcium compound weight ratio ranges from 60:40 to 70:30.

8. The sensor of claim 1, wherein a biodegradable time of the film is adjusted depending on a silk fibroin-calcium compound weight ratio.

9. The sensor of claim 8, wherein a biodegradable time of the third layer is shorter than a biodegradable time of the first layer, and thus the biodegradable time of the first layer or the third layer is adjusted so that the first surface is adapted to be attached to the inner wall of the viscera and then the third layer is decomposed, wherein the biodegradable time of the film is time that the film takes to be completely biodegraded.

10. The sensor of claim 9, wherein the silk fibroin-calcium compound weight ratio of the first layer ranges from 80:20 to 85:15, and
the silk fibroin-calcium compound weight ratio of the third layer ranges from 60:40 to 70:30.

11. The sensor of claim 1, wherein the sensor is expanded or contracted as the viscera is expanded or contracted,
a position of the metal generated corresponding to the expansion or contraction of the sensor is changed, and
a signal reflected by the metal is changed in response to the position of the metal,
wherein the signal is an ultrasonic wave or an electromagnetic wave.

12. The sensor of claim 1, wherein the viscera is any one of a stomach, an intestine, a bladder, and a womb.

13. A method for measuring compliance of viscera performed by a detection apparatus, comprising:
transmitting a signal to the sensor of claim 1, the sensor attached to inner wall of the viscera;
receiving the signal reflected from the sensor; and
measuring the compliance of the viscera to which the sensor is attached based on the received signal,
wherein the sensor includes a first layer having a first surface and a second surface opposite to the first surface, a second layer having a third surface attached to the second surface and a fourth surface opposite to the third surface and adapted to expand or contract as the viscera is expanded or contracted, and a third layer having a fifth surface attached to the fourth surface and a sixth surface opposite to the fifth surface and adapted to be attached to a catheter,
each of the first layer, the second layer, and the third layer includes silk fibroin and a calcium compound,
the sensor is adapted to be inserted into an interior of a body,
the first surface is adapted to be attached to the inner wall of the viscera for maintaining the sensor in the viscera after the catheter is detached from the sensor and removed from the viscera,
the second layer has a marker made of at least two metals and inserted into the film, and
each metal of the at least two metals is inserted into a different edge part of the film.

14. The method of claim 13, wherein the transmitting of the signal is performed plural times, and
the transmitting of the signal is performed plural times and thus the plurality of reflected signals received are analyzed to measure how much the sensor is expanded or contracted to measure the compliance of the viscera.

15. The method of claim 13, wherein the signal is an ultrasonic wave.

* * * * *

UNITED STATES PATENT AND TRADEMARK OFFICE
CERTIFICATE OF CORRECTION

PATENT NO. : 10,405,788 B2  
APPLICATION NO. : 15/937786  
DATED : September 10, 2019  
INVENTOR(S) : Lee et al.

Page 1 of 1

It is certified that error appears in the above-identified patent and that said Letters Patent is hereby corrected as shown below:

In the Claims

Claim 3, Column 12, Line 58, please delete "when a silk" and insert --when the silk--.

Signed and Sealed this  
Third Day of December, 2019

Andrei Iancu  
*Director of the United States Patent and Trademark Office*